United States Patent
Saurat et al.

(10) Patent No.: US 6,296,644 B1
(45) Date of Patent: Oct. 2, 2001

(54) SPINAL INSTRUMENTATION SYSTEM WITH ARTICULATED MODULES

(76) Inventors: Jean Saurat, 5 allee des Rochers, 49240 Avrille (FR); Jose Vicente Barbera Alacreu, D.N.I. 19.396.024, C/Santa Amalia, 2B, 24, 49009 Valencia (ES)

( * ) Notice: Subject to any disclaimer, the term of this patent is extended or adjusted under 35 U.S.C. 154(b) by 0 days.

(21) Appl. No.: 09/513,557

(22) Filed: Feb. 25, 2000

Related U.S. Application Data

(63) Continuation of application No. PCT/IB98/01328, filed on Aug. 26, 1998.

(51) Int. Cl.[7] .................................................. A61B 17/70
(52) U.S. Cl. ............................................................. 606/61
(58) Field of Search .................................. 606/61, 60, 72

(56) References Cited

U.S. PATENT DOCUMENTS

| | | | | |
|---|---|---|---|---|
| 3,846,846 | * | 11/1974 | Fischer | 606/72 |
| 3,858,578 | * | 1/1975 | Milo | 600/229 |
| 5,387,213 | | 2/1995 | Breard et al. | |
| 5,507,826 | | 4/1996 | Besselink et al. | |
| 5,551,871 | | 9/1996 | Besselink et al. | |
| 5,649,925 | * | 7/1997 | Barbera Alacreu | 600/61 |
| 5,766,004 | | 6/1998 | Besselink et al. | |

FOREIGN PATENT DOCUMENTS

| | | |
|---|---|---|
| 94 02 695.5 | 4/1994 | (DE) . |
| 0 696 440 A1 | 2/1996 | (EP) . |
| 2 081 766 A1 | 3/1996 | (ES) . |
| 2 697 428 A1 | 5/1994 | (FR) . |
| 2 715 825 A1 | 8/1995 | (FR) . |

* cited by examiner

*Primary Examiner*—Jeffrey A. Smith
*Assistant Examiner*—Eduardo C. Robert
(74) *Attorney, Agent, or Firm*—Woodard, Emhardt, Naughton Moriarty & McNett

(57) ABSTRACT

This spinal osteosynthesis instrumentation comprises at least two modules (1, 2) articulated together by a male-female spherical connection (5, 8) permitting a relative orientation of the modules in all directions, and ring (14) for rigidifying the assembly of the modules (1, 2) in the desired orientation so as to adapt it to the anatomy of the considered spinal segment. The modules (1, 2) each comprise a body (3) in which is formed a spherical socket (5) opening onto an end of the body, and a spherical head or ball (8) of an adjacent module can be inserted in this socket and maintained therein by a clipping action thereby forming a ball joint. This articulated system is extremely flexible and can be easily adapted to the anatomies of the spinal segments without exerting a substantial force on the patient, and can be maintained with the desired angulation by use of rings (14) clamping the articulated connections and composed of an alloy having a shape memory which clamp the balls (8) at the temperature of the body of the patient.

49 Claims, 4 Drawing Sheets

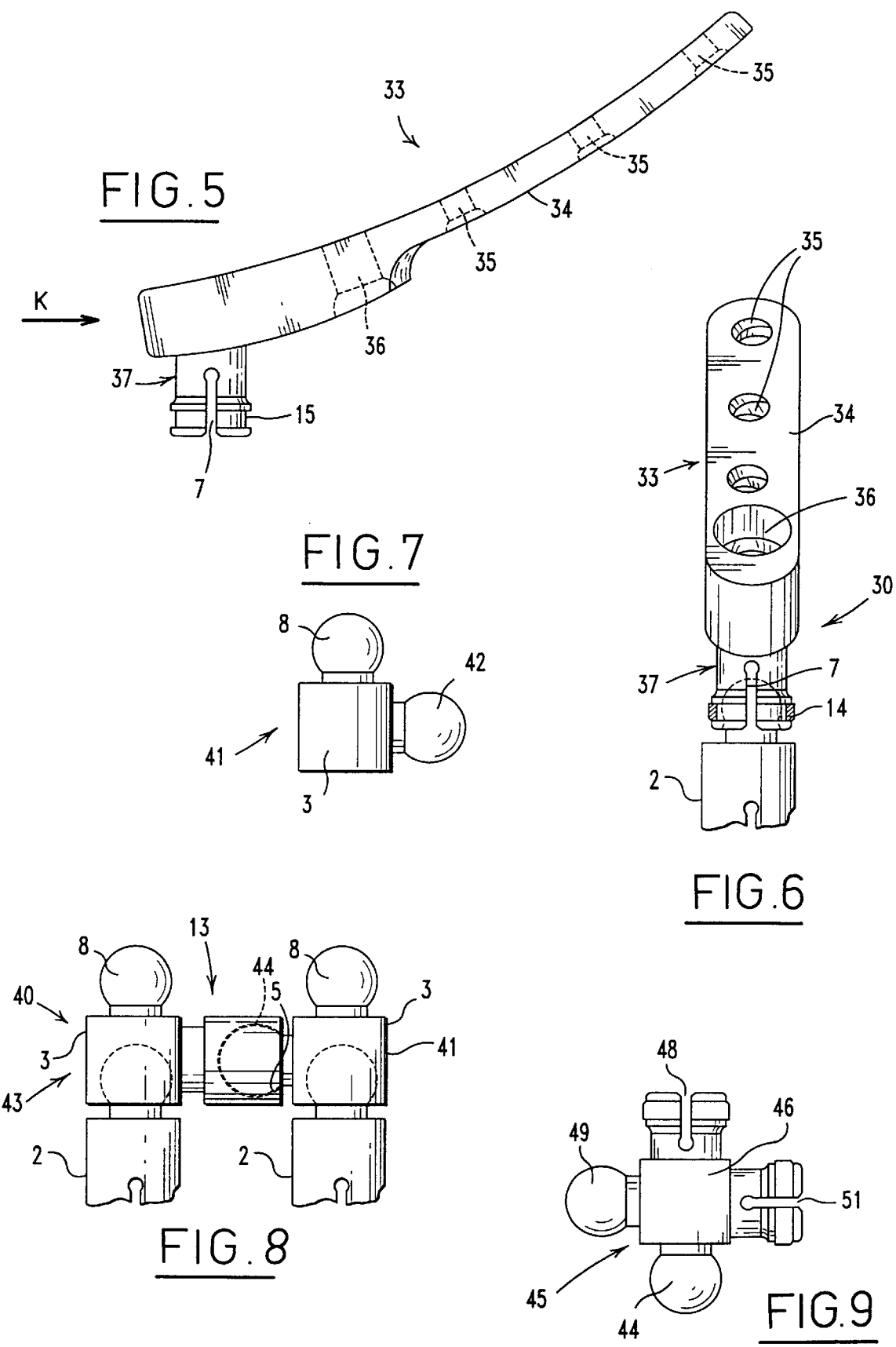

SPINAL INSTRUMENTATION SYSTEM WITH ARTICULATED MODULES

This is a continuation of application No. PCT/IB98101328, filed on Aug. 26, 1998. Now international publication number WO 99/09902.

TECHNICAL FIELD

The present invention relates to a spinal osteosynthesis instrumentation adapted to stabilize at least a part of the spine.

BACKGROUND

As is known, spinal osteosynthesis devices usually comprise vertebral rods which are rigid and bent so as to adapt them to the anatomy of the considered spinal segment, bone anchorage means formed by screws or pedicle hooks, and connecting elements between these anchorage means and the rods. Sometimes the rods are interconnected by transverse connecting devices.

The bending of the rods in two planes (sagittal plane and frontal plane) is a complex operation difficult to properly carry out outside the patient. When this bending operation is carried out on the patient during the surgical intervention, it is also a difficult undertaking and not free from risk for the patient. Moreover, such devices require a large number of parts which considerably increases the time required for the surgical intervention and renders them costly. Naturally, it is desirable to decrease the length of such surgical procedures to reduce the risk posed to the patient and to accordingly reduce associated costs.

In order to overcome these drawbacks, a system has been proposed in Spanish patent application No. 940 10/5 to Barbera Alacreu, filed May 13, 1994, which comprises a plurality of pins fitted one inside the other in pairs so as to form a kind of articulated chain. These pins are provided with anchorage hooks and are traversed longitudinally by a cable for maintaining the assembly under tension in the desired position. When the cable is put under tension, the pins are locked together by friction.

However, such a device has various notable drawbacks. For example, it requires a very high tension to obtain a good adherence or grip between the surfaces in contact. Further, the cable must be fixed at its end by a setting or forming-over operation which requires a high degree of skill to effectively carry out in the operating theatre. Lastly, in the event of breakage of the cable, the assembly of the pins is no longer maintained and the device collapses, which is a particularly serious risk for the patient.

Thus, there is a need for a spinal stabilization system that may be more readily shaped to conform to desired contours in the sagittal and frontal planes. Preferably, such multidimensional shaping may be easily performed and still provide a rigid stabilization construct once the desired shape is attained. The present invention meets these needs and has other significant advantages and benefits.

DISCLOSURE OF THE INVENTION

In one form of the present invention, a spinal osteosynthesis apparatus includes a first module having a ball and a second module having a socket receiving the ball therein. Also included is a clamping member element disposed on the second module that is made of a shape memory material. The clamping member permits relative motion of the ball in the socket when at a first temperature to correspondingly position the first module relative to the second module. Further, the clamping member clamps the ball within the socket to provide a generally rigid assembly of the first module and the second module when at a second temperature greater than the first temperature. This form permits contouring the modules to a desired shape while the clamping member is at the first temperature and raising temperature to the second temperature to retain the shape. Preferably, the first temperature is less than about 20 degrees Celsius and the second temperature is greater than about 20 degrees Celsius. More preferably, the second temperature is about the nominal body temperature of a human patient.

In an additional form of the present invention, a spinal osteosynthesis apparatus includes a first module having a ball at one end and a second module defining a socket receiving the ball therein. The second module is elastically deformable to receive the ball in the socket by a clipping action and retain the ball in the socket. The second module is configured to permit positioning of the first module relative to the second module while the ball is retained in the socket and to selectively fix the ball in the socket to provide a generally rigid assembly. At least one of the first and second modules carries a bone anchorage element configured to engage a patient's spine.

In a further form of the present invention, a spinal osteosynthesis apparatus includes a first chain of a first number of articulated modules connected together by a corresponding first number of ball-and-socket joints. A first one of the first modules includes a first hook configured to engage a patient's spine, and a second one of the first modules defines a first opening configured to receive a first threaded fastener for engaging the patient's spine. The apparatus also includes a second chain of a second number of articulated modules connected together by a corresponding second number of ball-and-socket joints. A first one of the second modules includes a second hook configured to engage the patient's spine and a second one of the second modules defines a second opening configured to receive a second threaded fastener for engaging the patient's spine. A third one of the first modules is transversely connected to a third one of the second modules by a ball-and-socket joint laterally disposed between the first and second chains.

In a further form, the spinal osteosynthesis instrumentation comprises two independent modules, means for ensuring a retaining connection between the modules enabling them to be oriented in all directions, means for connecting the modules to a bone, and means for immobilizing the modules relative to each other, the instrumentation permitting effecting a correction and then a final immobilization.

In another form of the present invention, the instrumentation comprises at least two modules provided with bone anchorage elements articulated together by a male-female spherical connection permitting a relative orientation of the modules in all directions, and means for rigidifying the assembly of the modules in the desired orientation so as to adapt the assembly to the anatomy of the considered spinal segment. The instrumentation according to the invention thus constitutes an assembly of a plurality of modules articulated together in pairs, which permits arranging them to conform in a multidirectional manner to the spine of the patient in the manner of an articulated chain, with no force exerted on the spine and with the assembly exactly conforming to the anatomy of the latter. Once this chain has been put into shape in the desired position, it can be maintained rigidly in this configuration by suitable means.

In still another form, some sections of the articulated chain may be rendered rigid while others remain freely articulated to permit corrections in situ, which is not generally available when bent rigid rods are employed. In this way, corrections can be effected and then the assembly can be finally immobilized. The bone anchorage may be ensured by any adapted means such as: threads, cables, ligaments, cages, rods, curved or flat plates, screws.

In yet another form of the invention, each module comprises a body in which is formed a spherical socket opening onto one end of the body for receiving a spherical head of an adjacent module, this head being maintained in its socket by a clipping action, thereby forming a ball joint. One or more of the modules of the instrumentation may comprise a body and a spherical articulation head in one piece with the body, the latter having for example a substantially cylindrical outer surface which imparts to the module the appearance of a pawn or a kind of skittle. One or more modules may be equipped laterally with a bone anchorage hooking strip, or a plate receiving a bone screw.

According to another advantageous feature of the invention, rigidifying means for the connections between the modules comprise rings composed of a shape memory alloy. The rings are adapted to surround the corresponding bodies in the region of their sockets for articulation to the neighboring modules, and exert on the walls of the sockets and the spherical head inserted therein a clamping action at the temperature of the body of the patient by a shrinkage of the rings, these rings expanding at a lower temperature. These clamping rings therefore benefit from the characteristics of the shape memory of some alloys which, at low temperature, for example at 10 to 20° C., are relatively soft and in the expanded state, and at a higher temperature, for example at the temperature of the human body (37° C.), become shrunk and consequently exert a very high clamping force on the part they surround.

The instrumentation according to the invention thus permits replacing the vertebral rods employed up to the present time for the staying of the spine by such articulated assemblies. Among the advantages of this instrumentation over rigid rods, is the capability of very closely conforming to the anatomy of the spinal segment rapidly and with minimum difficulty. This segment may be for example a cervical region, a thoracic region, a lumbar region, or a sacral region.

Accordingly, one object of the present invention is to provide a spinal osteosynthesis instrumentation that may be readily conformed to a desired shape.

Another object is to provide a means of making a chain of articulated modules rigid once a desired shape of the modules is attained.

Yet another object of the present invention is to provide a spinal instrumentation system with articulated modules adapted for engagement to a patient's spine by hooks and threaded fasteners.

Further objects, benefits, aspects, forms, features, and advantages of the invention will appear from the following description with reference to the accompanying drawings which illustrate several embodiments of the invention by way of non-limitative examples.

BRIEF DESCRIPTION OF THE DRAWINGS

FIG. 5 is a side elevational view of still another module type of the instrumentation according to the invention.

FIG. 6 is an elevational view in the direction of arrow K of FIG. 5 of the module shown in FIG. 5 assembled to another module of a different type.

FIG. 7 is an elevational view of a further module type provided with a lateral sphere for forming an articulation with another module.

FIG. 8 is an elevational view of an additional module type assembled with the module shown in FIG. 7 and modules shown in FIGS. 1–3.

FIG. 9 is an elevational view of yet another module type of the present invention.

MODE(S) FOR CARRYING OUT THE INVENTION

Figure 1:
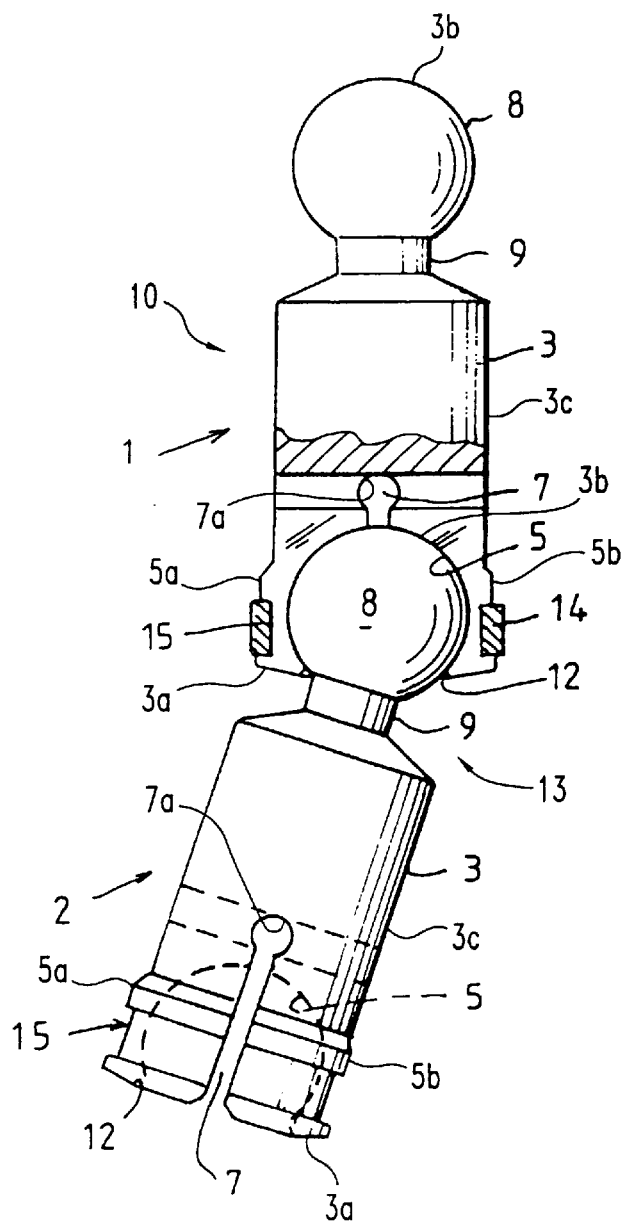
FIG. 1 is an elevational view partly in section to a larger scale of a first embodiment of two modules of a spinal osteosynthesis instrumentation assembly of the invention, these modules being articulated to each other.

The instrumentation illustrated in the drawings is used for a spinal osteosynthesis, preferably for stabilizing a spinal segment in the desired position and if need be to correct vertebral deformations. As illustrated in FIG. 1, this instrumentation comprises an assembly 10 of at least two modules 1, 2 articulated together by a male-female spherical connection. Each module 1, 2 comprises a body 3, having end 3*a* in which is formed a spherical socket 5. Socket 5 opens onto end 3*a* of body 3. At the end 3*b* removed from socket 5, each body 3 is extended by a spherical head or ball 8 attached by neck 9. Each body 3 has a central portion 3*c* generally having a cylindrical shape and is disposed between the opposing ends 3*a*, 3*b*. Preferably, body 3 comprising socket 5, head 8, and neck 9 is integrally formed as one piece. Formed in the opposing walls 5*a*, 5*b* of each socket 5 are at least two diametrally opposed longitudinal slots 7 which impart to walls 5*a*, 5*b* a certain flexibility enabling them to be spread apart when ball 8 of another module is inserted in socket 5. Slots 7 generally extend further along the longitude of body 3 than socket 5 and terminate in a generally circular opening 7*a* adjacent the innermost margin of socket 5.

The entire edge of each spherical socket 5 is advantageously provided with a respective annular chamfer 12 which is outwardly divergent so as to define a point of increased resistance to the passage of the ball 8 which, in association with the flexibility of walls 5*a*, 5*b* of socket 5, permits the insertion and the maintenance of ball 8 by a clipping action in socket 5. The ball 8 consequently forms the ball of a ball-and-socket joint 13 between the two modules 1, 2.

It is consequently possible to form an articulated assembly 10 of modules 1 or 2 connected one to the next by ball 8 and socket 5, which enables each module 1, 2 to be oriented in all directions within a cone of a given angular amplitude. Said differently, this arrangement permits orientation of module 1 relative to module 2 by rotation about any of three mutually perpendicular axes.

The instrumentation further comprises means for rigidifying or fixing the connections between the modules 1, 2. Preferably, these means comprise clamping members in the form of rings 14 composed of an alloy having a memory of its shape that is adapted to surround the corresponding bodies 3 of the modules 1, 2 in the region of their spherical sockets 5. Each clamping ring 14 is at least partly disposed in a corresponding groove 15 provided on the outer periphery of walls 5a, 5b of socket 5.

The alloy making up each ring 14 has the feature called "shape memory", i.e. the alloy has the characteristics of being deformable by exertion of small forces when it is at low temperature, for example at room temperature (about 10 to 20° C.), and of shrinking and creating a clamping action on the surface with which the ring 14 is in contact when the temperature of the ring rises to the temperature of the body of the patient (about 37° C.). Therefore, each ring 14 has at this temperature a powerful clamping action on the walls of the socket 5, and consequently on the ball 8 disposed therein, and in this way firmly maintains the ball 8 in the chosen angular orientation relative to the socket 5 in which it has been placed. As a non-limitative example, the alloy having a shape memory may be of a nickel-titanium alloy, with the material of the bodies 3 then being titanium.

In the embodiment illustrated in the drawings, the bodies 3 are in the form of small pawn-like pins or skittles inserted one inside the other. In other words, bodies 3 each generally have the shape of a bowling pin. An articulated chain of modules 1, 2 may be advantageously substituted for the vertebral rods used up to present time in spinal osteosynthesis devices. A corresponding number of ball-and-socket joints 13 connect the modules 1,2 of the chain together.

Figure 2:
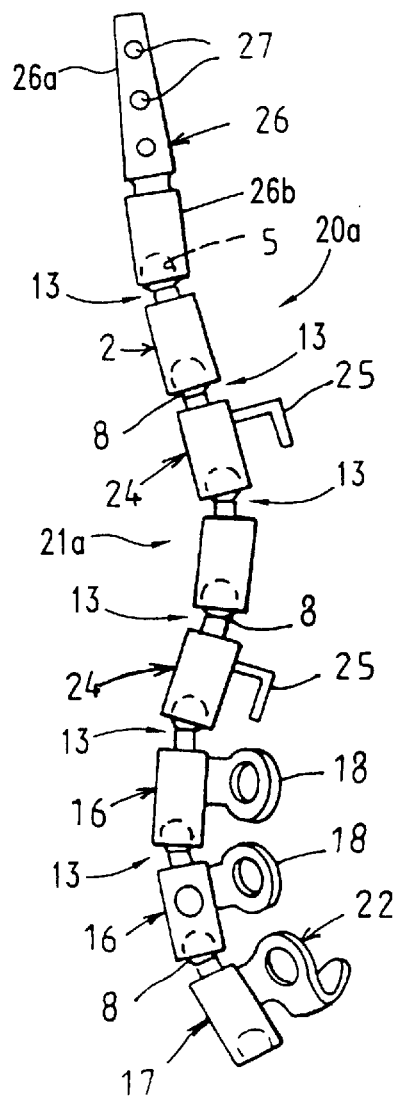
FIG. 2 is a simplified plan view of a spinal osteosynthesis instrumentation comprising an assembly of articulated modules in a second embodiment comprising several different types of modules.
Figure 3:
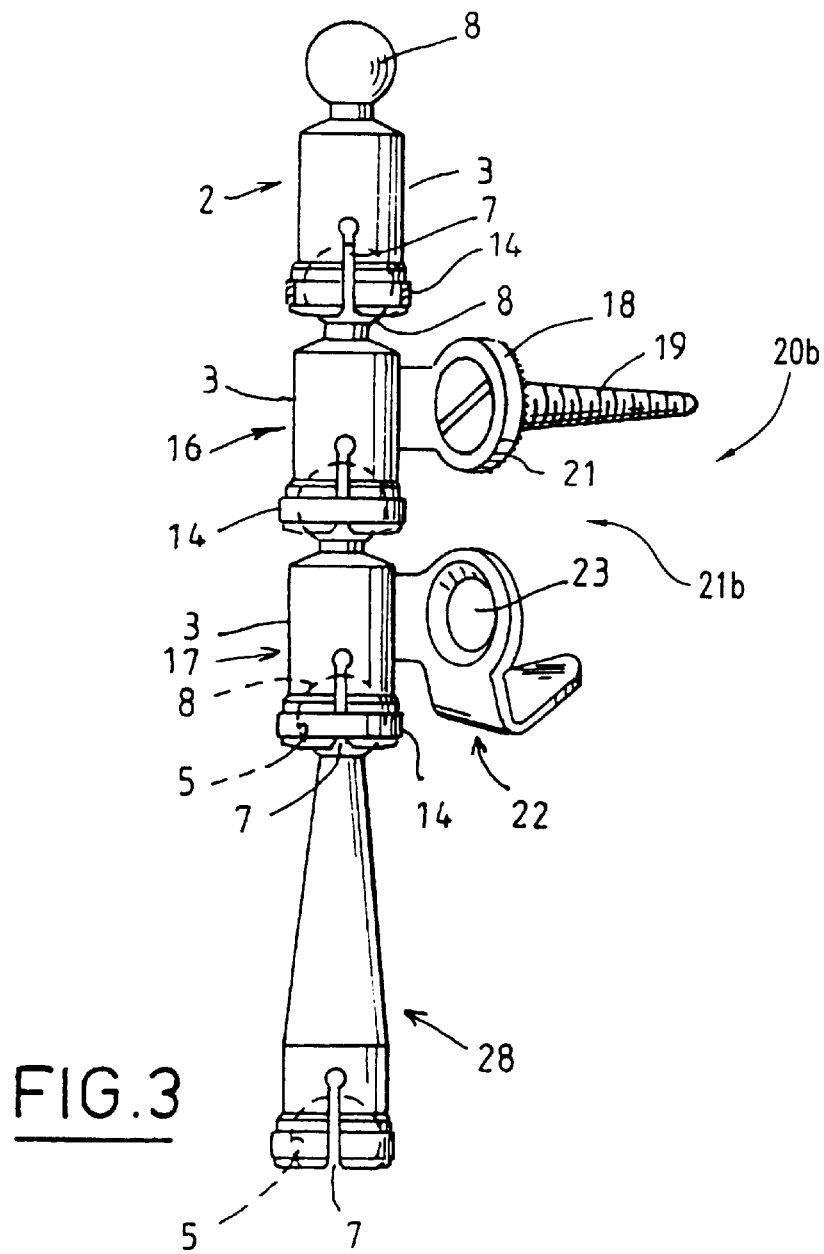
FIG. 3 is a plan view to a larger scale of a third embodiment of the spinal osteosynthesis instrumentation according to the invention comprising four modules.

Modules 1, 2 may be adapted to provide means for fixing them to the vertebral bodies of the spine, cranial bone, or other bone; and incorporated into an articulated module chain, such as chain 21a of instrumentation assembly 20a shown in FIG. 2 or chain 21b of instrumentation assembly 20b shown in FIG. 3. For example, chains 21a, 21b include spinal modules 16 whose bodies and balls are identical to those of the modules 1 and 2 but are provided with lateral means for permitting a bone anchorage. This lateral means for each module 16 includes a lateral ring 18 which may receive a threaded fastener, such as anchorage screw 19 (FIG. 3) or a bolt/nut assembly (not shown), and may be provided on one of its faces with radial splines 21 (FIG. 3) for cooperation with a plate which is also splined (not shown). Details concerning slots 7, clamping rings 14, and grooves 15 are not shown in FIG. 2 to preserve clarity.

In another example, chains 21a, 21b each include module 17. Module 17 includes a lateral hook 22 in which an opening 23 is formed for the passage of a screw (not shown). In yet another example in chain 21a of FIG. 2, module 24 is provided with another form of hook designated by reference number 25. One or more modules 26 may also be included, as shown in assembly 20a. Module 26 has plate 26a provided with openings 27 for the passage of threaded bone anchorage fasteners such as screws or a bolt/nut arrangement. Plate 26a is extended by body portion 26b. Body portion 26b defines a spherical socket 5 in which a ball 8 of the neighboring module, for example a module 2 (FIG. 2), may be inserted to form a corresponding ball-and-socket joint 13. Preferably, the number and location of the bone engaging module types in a given chain, such as modules 16, 17, 24, 26, depends on the region of the spine in which it is to be positioned.

Each module 1, 2, 16, 17, 24, 26 extends over a length which may be either the intervertebral distance in the corresponding region of the spine, a multiple of this distance, or any other length. Thus in FIG. 3, for instance, assembly 20b comprises an articulated chain 21b with module 28. Module 28 has ball 8, socket 5, and slots 7 with an overall length substantially double the length of modules 1, 2, 16, 17, 24, or 26. In one preferred embodiment, modules 1, 2, 16, 17, 24, 26 correspond to a desired intervertebral distance and module 28 corresponds to generally twice this distance.

Figure 4:
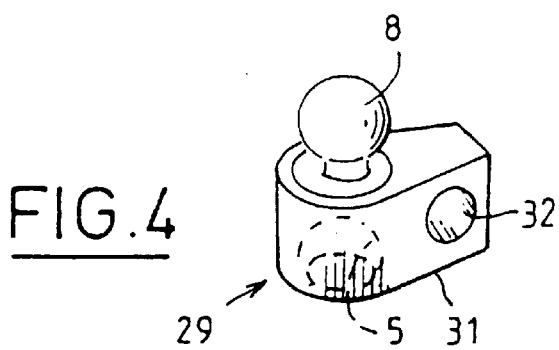
FIG. 4 is a perspective view to a larger scale of another module type of the instrumentation according to the invention.

The module 29 of FIG. 4 has a massive body 31 in which a tapped hole 32 is formed for the passage of a screw (not shown). Hole 32 is laterally positioned relative to socket 5 and ball 8 of module 29. Module 29 may be incorporated into an articulated chain, such as chain 21a or 21b either in place of or in addition to existing modules; or into any other chain configuration as would occur to those skilled in the art.

In another embodiment, a chain terminates with at least one module 33 (FIGS. 5 and 6). Module 33 has bent plate 34 provided with a plurality of openings 35, 36 for the passage of screws or other threaded fasteners (not shown) and completed at one of its ends by a body 37 similar to the bodies 3, but devoid of ball 8. The body 37 is in fact connected to the plate 34 by any suitable means known to those skilled in the art to provide one integral piece. Preferably, module 33 has a curvature adapted to the shape of the occiput or the sacrum. In FIG. 6, module 33 is shown connected to module 2 to form assembly 30. Module 2 is only partially shown and is preferably connected to other modules 1, 16, 17, 24, 26, 28 or 29 to form a desired chain of articulated modules.

The occipital and sacral plates, such as 33, are more easily adaptable to the anatomy of the patient than a conventional plate having pre-machined openings in respect of which the position of the screws is imposed. Indeed, the articulation bodies 37, of these plates allow an angulation which considerably increases their flexibility of adaptation to the optimal fastening position.

The variant of FIG. 7 is a module 41 provided with a lateral ball 42 permitting a transverse articulation with another module, such as module 43 of FIG. 8. Module 43 comprises a part (3, 8) identical to the modules 1 and 2 (as does module 41), but is provided with a second tubular body 44 projecting laterally from body 3. Formed in the body 44 is spherical socket 5 permitting a transverse articulation of the module 43 on the module 41 by insertion of the ball 42 in socket 5 of the body 44. FIG. 8 further shows assembly 40 with module 43 and module 41 connected by a corresponding ball-and-socket joint 13 therebetween. The modules 41 and 43 permit transversely interconnecting two articulated chains extending along a spinal segment. Assembly 40 also includes connections of modules 41, 43 to corresponding modules 2 (partially shown).

The module 45 of FIG. 9 is provided with four means of connection to other elements arranged in a cross around its body 46: a sphere 47 and a spherical socket 48 at its opposite ends, a sphere 49 and a spherical socket 51 provided laterally.

Figure 10:
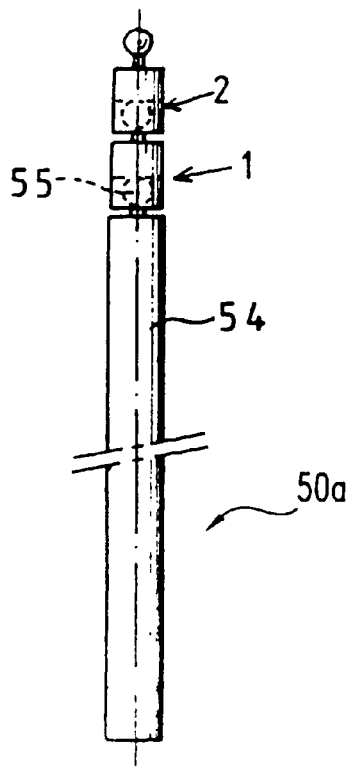
FIGS. 10 and 11 are elevational views of a fourth and fifth embodiment of the instrumentation according to the invention.

FIG. 10 shows instrumentation 50a of another embodiment. Instrumentation 50a includes rigid rod 54 provided with sphere 55 at one end. Sphere 55 is articulated to module 1 which is itself articulated to a module 2 in instrumentation 50a.

Figure 11:
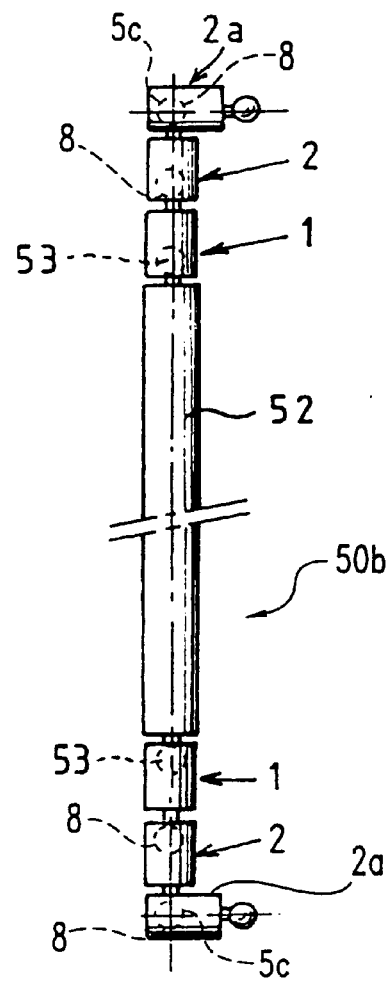

The embodiment of FIG. 11 shows instrumentation 50b. Instrumentation 50b comprises a rigid vertebral rod 52, which is smooth or has asperities and is provided with two spheres 53 at its opposite ends. Spheres 53 are articulated to modules 1, 2, 2a which are themselves articulating in pairs; the end module 2a may be disposed perpendicularly to the modules 1, 2 and rod 52. End module 2a has socket 5c opening laterally.

Figure 12:
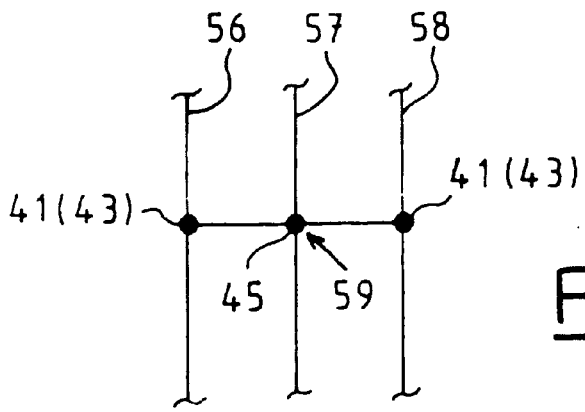
FIG. 12 is a diagrammatic elevational view of a sixth embodiment of the instrumentation comprising three articulated assembling chains.

The assembly of FIG. 12 comprises three chains 56, 57, 58 formed of articulated modules and connected by a transverse connection 59. The chains 56, 57, 58 may alternatively or additionally include rigid rods such as rods 52 and 54. The crossing of the rod or central chain 57 with the transverse connection 59 is provided by means of a module having four articulation elements such as the module 45 (FIG. 9). On the other hand, modules having three articulation elements such as 41 or 43 are sufficient for the connection of the transverse connection to the lateral rods or chains 56, 58.

The modules 1, 2 of the instrumentation according to the invention may be constructed in accordance with numerous embodiments. For example, modules of a single articulation embodiment have only a ball or a spherical socket. In embodiments having two articulation elements, the module has two balls, two sockets, or one ball and one socket. Three articulation element embodiments include modules with one ball and two sockets, or two balls and one socket. Four articulation element embodiments include modules with two balls and two spherical sockets, one ball and three sockets, three balls and one socket, and the like.

The invention permits pre-assembling a series of modules, with or without bone anchorage elements, adapted without difficulty to the anatomy of the patient, then locking the assembly in the chosen angulations so as to maintain the reduction. It will be understood that such an articulated system remains mobile, and therefore adjustable, so long as the clamping members constituted by the rings 14 are not activated. The device may be assembled either on the patient or outside the patient and then anchored to vertebral bodies of a patient's spine, either before an angular clamping by the rigidifying means 14, or after this angular clamping, as the surgeon desires.

Each clamping ring 14 is preferably pre-engaged on the corresponding module in the cold state in which it is flexible between about 10 and 18° C. (temperature of the operating theatre). To clamp the modules at the chosen angulation, the rings 14 are heated by a hot liquid and thereafter maintained at the patient's body temperature. In alternative embodiments, the rigidification of the articulated assembly with angulations between the modules could be obtained by means of rings slipped over the bodies with force or secured by a fastener such as a screw, instead of the shrinkable rings 14 of an alloy having a shape memory.

In addition, the various modules 1, 2, 16, 17, 24, 26, 29, 33, 41, 43, 45 and rods 52, 54 may be coupled together in a chain in any suitable sequence or quantity, and combined with other module types as would occur to those skilled in the art. Further one or more such chains may be interconnected to provide a desired instrumentation as would occur to those skilled in the art.

The instrumentation according to the invention is extremely flexible since it is easily adaptable to the anatomy of all the regions of the spine. In this way, the difficult and complex operations for bending the vertebral rods of the instrumentations of the prior art are avoided, with the use of a smaller number of parts. Further, the connections between the modules by means of clamping rings having a shape memory avoid the necessity to effect setting or forming-over operations. Another important advantage of this instrumentation resides in the fact that, in the event of fracture of a module, the overall assembly with the spine remains, which is essential for the safety of the patient. Indeed, in the event of fracture of a ring 14, the two modules concerned remain assembled owing to the clipping action which maintains the articulation ball 8 in its socket, and the maintenance of the overall assembly is not jeopardized.

French Patent Application Number 97 10722 filed Aug. 27, 1998 to Barbera Alacreu, and to which priority is claimed, is hereby incorporated by reference as if it were specifically set forth in its entirety herein. While the present invention has been shown and described in detail in the drawings and foregoing description, the same is considered to be illustrative and not restrictive in character, it being understood that only the preferred embodiment have been shown and described and that all changes, modifications, and equivalents that come within the spirit of the invention as defined by the following claims are desired to be protected.

What is claimed is:

1. A spinal osteosynthesis apparatus, comprising:
a first module having a first ball;
a second module having a first socket receiving said first ball therein;
a clamping member disposed on said second module, said clamping member being made of a shape memory material; and
wherein said clamping member permits relative motion of said first ball in said first socket when at a first temperature to correspondingly position said first module relative to said second module, and said clamping member clamps said first ball within said first socket when at a second temperature greater than said first temperature to provide a generally rigid assembly of said first module and said second module.

2. The apparatus of claim 1, wherein said second module includes a groove defined about said socket, and wherein said clamping member is a ring of said shape memory material that engages said groove.

3. The apparatus of claim 2, wherein said second temperature is greater than about 20 degrees centigrade.

4. The apparatus of claim 2, wherein said second temperature is about body temperature of a human patient and the shape memory material is an alloy of titanium and nickel.

5. The apparatus of claim 2, wherein said first module has a second socket opposite said first ball.

6. The apparatus of claim 5, wherein said second module has a second ball opposite said first socket.

7. The apparatus of claim 6, wherein said first module has a generally cylindrically shaped central body portion connected to said ball by a neck.

8. The apparatus of claim 7, wherein said first socket is defined by at least two walls separated by at least two slots to render said walls flexible for insertion of said first ball.

9. The apparatus of claim 8, wherein said first socket is provided with an inclined annular chamfer configured for passage of said first ball therethrough with a clipping action.

10. The apparatus of claim 7, wherein said first module and said second module are configured in a first articulated chain of modules numbering at least four, each one of said modules being joined to another of said modules by a ball-and-socket joint.

11. The apparatus of claim 10, wherein said first chain is tranverseley connected to a second articulated chain of modules by a ball-and-socket joint therebetween.

12. The apparatus of claim 7, in one of said first and second modules includes a bone anchorage element configured to engage a patient's spine.

13. The apparatus of claim 12, wherein said bone anchorage element is from the group consisting of threaded elements and hooks.

14. The apparatus of claim 1, wherein said first module has a second socket opposite said first ball.

15. The apparatus of claim 1, wherein said second module has a second ball opposite said first socket.

16. The apparatus of claim 1, wherein said first module has a generally cylindrically shaped central body portion connected to said ball by a neck.

17. The apparatus of claim 1, wherein said first socket is defined by at least two walls separated by at least two slots to render said walls flexible for insertion of said first ball.

18. The apparatus of claim 1, wherein said first socket is provided with an inclined annular chamfer configured for passage of said first ball therethrough with a clipping action.

19. The apparatus of claim 1, wherein said first module and said second module are configured in a first articulated chain of modules numbering at least four, each one of said modules being joined to another of said modules by a ball-and-socket joint.

20. The apparatus of claim 19, wherein said first chain is transversely connected to a second articulated chain of modules by a ball-and-socket joint therebetween.

21. The apparatus of claim 19, wherein one of said modules includes a bone anchorage element.

22. The apparatus of claim 19, wherein one of said modules in said first articulated chain of modules is a rod, said rod having an end and a ball attached to said end.

23. The apparatus of claim 1, wherein one of said first and second modules includes a hook configured to engage a patient's spine.

24. The apparatus of claim 1, wherein one of said first and second modules includes a plate defining an opening therethrough, said opening being configured to receive a threaded fastener for engaging a patient's spine.

25. The apparatus of claim 24, wherein said plate is curved and defines a number of openings each configured to receive said threaded fastener for engaging the patient's spine.

26. The apparatus of claim 1, wherein said first module has a plurality of balls.

27. The apparatus of claim 26, wherein said first module has at least one socket, each of which is opposite a respective one of said balls.

28. The apparatus of claim 1, wherein said first module has a body, said body having a hole therethrough adapted to accommodate a bone anchorage element.

29. The apparatus of claim 28, wherein said hole is tapped.

30. The apparatus of claim 42, wherein said first ball has a longitudinal axis and said hole has a longitudinal axis, and said axes are non-intersecting.

31. The apparatus of claim 28, wherein said bone anchorage element is a threaded bone fastener.

32. The apparatus of claim 1, wherein said second module has a plurality of sockets.

33. The apparatus of claim 32, wherein said second module has at least one ball, each of which is opposite a respective one of said sockets.

34. A spinal osteosynthesis apparatus, comprising:
a first module having a first ball;
a second module defining a first socket, said first socket receiving said first ball therein, said second module being elastically deformable to receive said first ball in said first socket by a clipping action and to retain said first ball in said first socket, said second module being configured to permit positioning of said first module relative to said second module while said first ball is retained in said first socket and to selectively clamp said first ball in said first socket to provide a generally rigid assembly; and
wherein at least one of said first module and said second module carries a bone anchorage element configured to engage a patient's spine.

35. The apparatus of claim 34, wherein said second module is engaged by a clamping ring made of shape memory material to provide a clamping action at a temperature greater than 18 degrees centigrade.

36. The apparatus of claim 34, wherein said first module has a body terminating in said first ball and a second socket opposite said first ball.

37. The apparatus of claim 34, wherein said second module has a second ball opposite said first socket.

38. The apparatus of claim 34, wherein said first socket is formed by at least two walls separated by at least two slots to render said walls flexible for insertion of said first ball.

39. The apparatus of claim 34, wherein said first socket is provided with an inclined annular chamfer configured for passage of said first ball therethrough.

40. The apparatus of claim 34, wherein said first module and said second module are configured in a first articulated chain of modules numbering at least four, each one of said modules being joined to another of said modules by a ball-and-socket joint.

41. The apparatus of claim 40, wherein said first chain is transversely connected to a second articulated chain of modules by a ball-and-socket joint therebetween.

42. The apparatus of claim 34, wherein said bone anchorage element includes a hook configured to engage the patient's spine.

43. The apparatus of claim 34, wherein said bone anchorage element defines an opening in one of said first module and said second module, said opening being configured to receive a threaded fastener for engaging the patient's spine.

44. The apparatus of claim 43, wherein said bone anchorage element includes a plate defining said opening.

45. The apparatus of claim 43, wherein said plate is curved and defines a number of openings each configured to receive said threaded fastener for engaging the patient's spine.

46. A spinal osteosynthesis apparatus, comprising:
a first chain of a first number of articulated modules, said first modules being connected together by a corresponding first number of ball-and-socket joints, a first one of said first modules including a first hook configured to engage a patient's spine, and a second one of said first modules defining a first opening configured to receive a first threaded fastener for engaging the patient's spine;
a second chain of a second number of articulated modules, said second modules being connected together by a corresponding second number of ball-and-socket joints, a first one of said second modules including a second hook configured to engage the patient's spine, a second one of said second modules defining a second opening configured to receive a second threaded fastener for engaging the patient's spine; and
wherein a third one of said first modules is transversely connected to a third one of said second modules by a ball-and-socket joint laterally disposed between said first chain and said second chain.

47. The apparatus of claim 46, wherein each of said first and second modules includes a fixation element comprised of shape memory material.

48. The apparatus of claim 47, wherein said fixation element includes a ring made of said shape memory material.

49. The apparatus of claim 46, wherein at least one of said first chain and said second chain terminates in a plate defining a third opening, said third opening being configured to receive a third threaded fastener for engaging the patient's spine.

* * * * *